(12) United States Patent
Cho et al.

(10) Patent No.: US 10,995,117 B2
(45) Date of Patent: *May 4, 2021

(54) PEPTIDE FOR SKIN REGENERATION OR WOUND TREATMENT AND USE THEREOF

(71) Applicant: KINE SCIENCES CO., LTD., Seoul (KR)

(72) Inventors: Dae Ho Cho, Seoul (KR); Min Chan Gil, Seoul (KR); So Mi Lee, Gimpo-si (KR); Myun Soo Kim, Seoul (KR)

(73) Assignee: KINE SCIENCES CO., LTD., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/222,808

(22) Filed: Dec. 17, 2018

(65) Prior Publication Data

US 2019/0112336 A1    Apr. 18, 2019

Related U.S. Application Data

(63) Continuation-in-part of application No. 15/739,894, filed as application No. PCT/KR2017/002998 on Mar. 21, 2017, now Pat. No. 10,188,694.

(30) Foreign Application Priority Data

Mar. 23, 2016 (KR) .................. 10-2016-0034327

(51) Int. Cl.
| | |
|---|---|
| *C07K 7/06* | (2006.01) |
| *A61P 17/02* | (2006.01) |
| *C07K 7/08* | (2006.01) |
| *A61Q 19/02* | (2006.01) |
| *A61K 9/06* | (2006.01) |
| *A61Q 19/08* | (2006.01) |
| *A61K 8/64* | (2006.01) |

(52) U.S. Cl.
CPC ............ *C07K 7/06* (2013.01); *A61K 8/64* (2013.01); *A61K 9/06* (2013.01); *A61P 17/02* (2018.01); *A61Q 19/02* (2013.01); *A61Q 19/08* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 9,012,723 B2 * | 4/2015 | Guo | C07K 14/415 800/285 |
| 10,188,694 B2 * | 1/2019 | Cho | A61K 38/08 |
| 2006/0234210 A1 * | 10/2006 | Kenan | A61M 1/3633 435/5 |

FOREIGN PATENT DOCUMENTS

| | | |
|---|---|---|
| EP | 1486506 | * 12/2004 |
| KR | 10-1020658 B1 | 3/2011 |
| KR | 10-1092915 B1 | 12/2011 |
| KR | 10-1355385 B1 | 2/2014 |
| KR | 10-2015-0135743 A | 12/2015 |
| KR | 10-2016-0006994 A | 1/2016 |
| WO | 2014/109417 A1 | 7/2014 |

OTHER PUBLICATIONS

Paterson et al. "Repeated polyploidization of Gossypium genomes and the evolution of spinnable cotton fibres." Nature 492:423-427(2012). https://www.nature.com/articles/nature11798.*
UniProtKB. A0A0D2RAT4 (A0A0D2RAT4_GOSRA). Uncharacterized Protein (REGRTLVEL) of *Gossypium raimondii* (New World Cotton). Apr. 29, 2015.*

* cited by examiner

*Primary Examiner* — Maury A Audet
(74) *Attorney, Agent, or Firm* — MH2 Technology Law Group, LLP

(57) ABSTRACT

Provided is a novel peptide for skin regeneration or wound healing and a use thereof. The novel peptide not only promotes the wound healing by increasing the production amount of collagen in dermal fibroblasts but also has an excellent whitening effect by inhibiting the production amount of melanin and tyrosinase activity of melanoma cells, and consists of peptides having a very small size to minimize side effects according to administration of external substances of very small peptides. As a result, it is expected that the novel peptide can be used as an active substance that can replace existing skin regeneration or would therapeutic agents.

13 Claims, 8 Drawing Sheets

Specification includes a Sequence Listing.

US 10,995,117 B2

PEPTIDE FOR SKIN REGENERATION OR WOUND TREATMENT AND USE THEREOF

CROSS-REFERENCE TO RELATED APPLICATIONS

The instant application is a continuation-in-part of U.S. patent application Ser. No. 15/739,894 filed on Dec. 26, 2017, which is a national-stage application under 35 USC § 371 of international patent application No. PCT/KR2017/002998 filed on Mar. 21, 2017, and claims the priority to Korean patent application No. 10-2016-0034327 filed on Mar. 23, 2016, and the entire disclosures of the prior-filed applications are incorporated herein by reference.

TECHNICAL FIELD

The present invention relates to a peptide for skin regeneration or wound healing and a use thereof.

The present invention is achieved by the project number of 1711030975 under the support of the governmental department in Korea, the research management organization of the project is the Korea Research Foundation, the name of the research business is the discovery business of creative materials, the name of the research project is the development of biodegradable skin regeneration material based on the functional immune technology, and the research period is from Dec. 4, 2015 to Apr. 30, 2016.

BACKGROUND ART

The skin is a primary barrier of the human body and protects the organs in the body from stimulation caused by external environments such as a temperature, a change in humidity, ultraviolet rays, pollutants, and plays an important role in maintaining homeostasis such as regulation of body temperature. The keratin, which is located at the outermost part of the skin, is a tissue formed by a change in cells of the skin, and consists of completely dead cells. Coarse cell layers formed in the dermal connective tissue of the dermis have no vitality of cells toward the epidermis and are changed into solid and regular cell layers. The skin with this structure serves as a line of defense that protects the moisture of the body from the outermost side and defends the various substances input from outside. That is, when the surface of the skin is wounded, the rapid regenerating ability of the epidermis promotes the recovery of the wound, thereby preventing additional infection through the wound and reducing the scarring of the skin surface.

When the damaged skin tissue is reconstructed, various reactions are involved, and particularly, migration, proliferation, and differentiation of keratinocytes, detachment of damaged cells, and production of the epithelial tissue are involved. The process of wound healing is a very complex reaction involving various cells and factors, and first, the platelet is aggregated at the wound site and various cell proliferation factors such as a transfection factor, a platelet-derived proliferative factor, and an epithelial cell proliferative factor are released to stimulate vascular endothelium, phagocyte, fibroblast and epithelial cells, thereby promoting cell proliferation. At the same time, while these cells themselves self-secretively produce and secrete substances such as fibroblast proliferation, transforming growth factors, interleukin and other substances, the wound healing mechanism proceeds.

Currently, an epidermal growth factor (EGF), which is widely used as a wound therapeutic agent due to various activities, is either obtained by purification or obtained by overexpression in bacteria. It takes a lot of time, money, and labor to obtain by direct purification. Also, the over-expression method in the bacteria has a problem in that the recovery yield is very low due to the low expression level in the cells and proteolytic enzyme of the bacteria. In addition, the EGF has been reported to exhibit a low therapeutic effect on chronic wound sites, and it has been difficult to commercialize the EGF due to the high price to the efficiency due to a temperature and a short half-life due to the proteolytic enzyme.

Under such a background, development of a novel therapeutic agent having an effective therapeutic effect while minimizing side effects of conventional drugs for skin regeneration or wound healing has been required and has been actively studied (Korean Patent Publication No. 10-2015-0135743), but it is still not enough.

DISCLOSURE

Technical Problem

The present invention has been made in an effort to solve the above problems, and the present inventors have made intensive studies on formulations for skin generation or wound healing to prepare a peptide consisting of 15 amino acids or less and confirmed enhancement of the production amount of collagen of dermal fibroblasts, the production amount of melanin of melanoma cells and a tyrosinase activity inhibition effect when the peptide was treated, and completed the present invention based thereon.

An object of the present invention is to provide a peptide for skin regeneration or wound healing, consisting of amino acid represented by SEQ ID NO: 1 or 2.

Another object of the present invention is to provide a pharmaceutical composition for skin regeneration or wound healing, containing the peptide or a polynucleotide encoding the peptide as an active ingredient.

Yet another object of the present invention is to provide a health functional food/cosmetic composition for skin regeneration or wound healing, containing the peptide as an active ingredient.

However, technical objects of the present invention are not limited to the aforementioned purpose and other objects which are not mentioned may be clearly understood to those skilled in the art from the following description.

Technical Solution

In order to achieve the object, in one aspect, the present invention provides a peptide consisting of amino acid represented by SEQ ID NO: 1 or 2. The peptide may be synthetically produced.

In a preferred embodiment, an N- or C-terminal of the peptide may bind to a protective group which is selected from the group consisting of an acetyl group, a fluorenylmethoxy carbonyl group, a formyl group, a palmitoyl group, a myristyl group, a stearyl group, a polyethylene glycol (PEG) group, a methyl group, D-form peptide group, an amide group, an albumin group, a polysialic acid (PSA) group, a hydroxyethyl starch (HES) group, and a C12-C18 fatty acid group.

In another aspect, the present invention provides a pharmaceutical composition for skin regeneration or wound healing, containing the peptide or a polynucleotide encoding the peptide as an active ingredient.

In a preferred embodiment, the peptide may be contained at a concentration of 1 to 500 ng/ml.

In another preferred embodiment, the wound may be a gash.

In still another preferred embodiment, the composition may further include a pharmaceutically acceptable carrier.

In yet another aspect, the present invention provides a cosmetic composition for improving skin aging or wound, containing the peptide as an active ingredient.

In a preferred embodiment, the composition may be in the form of suspension, emulsion, paste, gel, cream, lotion, powder, wax or spray.

In another preferred embodiment, the composition may have a skin whitening activity.

In still another aspect, the present invention provides a method for skin regeneration or wound healing including administering the peptide to a subject.

In still yet another aspect, the present invention provides a use for skin regeneration or wound healing of the peptide.

Advantageous Effects

The novel peptide according to the present invention not only promotes the wound healing by increasing the production amount of collagen in dermal fibroblasts but also has an excellent whitening effect by inhibiting the production amount of melanin and tyrosinase activity of melanoma cells, and consists of peptides having a very small size to minimize side effects according to administration of external substances of very small peptides. As a result, it is expected that the novel peptide can be used as an active substance that can replace existing skin regeneration or would therapeutic agents.

MODES OF THE INVENTION

Figure 1:
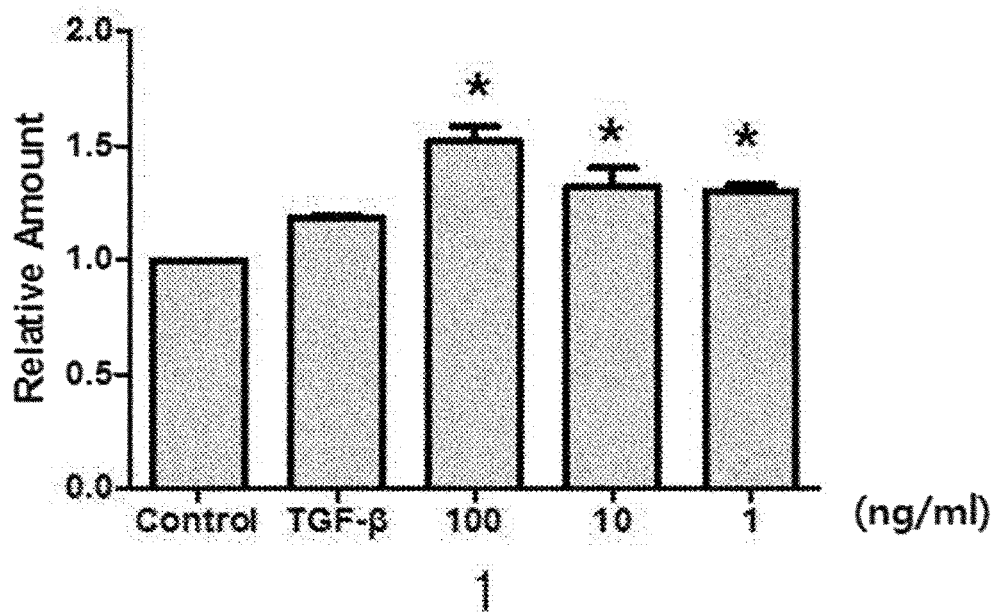
FIG. 1 illustrates a result of measuring an amount of procollagen produced from human dermal fibroblasts according to treatment of peptide 1 of the present invention.

Hereinafter, the present invention will be described in detail.

The present invention provides a peptide consisting of amino acid represented by SEQ ID NO: 1 or 2.

In the present invention, the "peptide" refers to a polymer consisting of two or more amino acids linked by an amide bond (alternatively, a peptide bond) and refers to a peptide having skin regeneration or wound healing activity for the purpose of the present invention. Despite various studies on a peptide therapeutic agent, there is a disadvantage that the peptide is too large in self-size to effectively introduce target tissues or cells, or has a short half-life and disappears in the body in a short period. As a result, the present invention has a technical meaning in that a novel peptide consisting of 20 amino acids or less while having an effective therapeutic effect is first established.

The peptide of the present invention may consist of amino acid represented by SEQ ID NO: 1 or 2, and may include an amino acid sequence having sequence homology with the amino acid sequence represented by SEQ ID NO: 1 or 2 of 75% or more, preferably 80% or more, more preferably 90% or more and most preferably 95% or more, and may additionally include an amino acid sequence prepared for the specific purpose of increasing a targeting sequence, a tag, a labeled residue, half-life, or peptide stability.

Further, the peptide may include a functional variant for the peptide of the present invention. The functional variant includes biological equivalents of a peptide sequence (SEQ ID NOS: 1 or 2) disclosed in the present specification. For example, additional modifications in amino acid or polynucleotide sequence of the peptide may be made to further improve the binding affinity and/or other biological properties of the peptide. Such modifications include deletion, insertion, and/or substitution of amino acid sequence residues of the peptide and are performed based on the relative similarity of amino acid side chain substituents, for example, hydrophobicity, hydrophilicity, charge size, and the like. By analysis of the size, shape and type of amino acid side chain substituents, it can be seen that arginine, lysine and histidine are all positively charged residues; alanine, glycine and serine have similar sizes; and phenylalanine, tryptophan and tyrosine have similar shapes. Accordingly, based on these considerations, arginine, lysine and histidine; alanine, glycine and serine; and phenylalanine, tryptophan and tyrosine may refer to biologically functional equivalents.

In addition, the peptide of the present invention may be obtained by various methods well known in the art. For example, the peptide may be prepared by polynucleotide recombination and protein expression systems or synthesis in vitro through chemical synthesis such as peptide synthesis, and cell-free protein synthesis.

In addition, to obtain better chemical stability, enhanced pharmacological properties (half-life, absorbency, potency, efficacy, etc.), altered specificity (e.g., broad biological activity spectrum), and reduced antigenicity, a protective group may bind to an N- or C-terminal of the peptide. Preferably, the protective group may be an acetyl group, a fluorenylmethoxycarbonyl group, a formyl group, a palmitoyl group, a myristyl group, a stearyl group, a polyethylene glycol (PEG) group, a methyl group, D-form peptide group, an amide group, an albumin group, a polysialic acid (PSA) group, a hydroxyethyl starch (HES) group, or a C12-C18 fatty acid group, but may include any ingredient capable of enhancing modification of the peptide, particularly, stability of the peptide, without limitation. The term "stability" used in the present invention refers to storage stability (for example, room-temperature storage stability) as well as in-vivo stability that protects the peptide of the present invention from attack of a protein cleavage enzyme in vivo.

In the present invention, "polynucleotide" is a polymer to which a nucleotide binds, and serves to transmit genetic information. For the purpose of the present invention, the polynucleotide encodes the peptide of SEQ ID NO: 1 or 2 and may include a polynucleotide sequence encoding the peptide and a sequence having sequence homology of 75% or more, preferably 85% or more, more preferably 90% or more, and most preferably 75% or more.

The term "homology" used in the present invention is to indicate a similar degree to a wide-type amino acid sequence or a polynucleotide sequence, and the comparison of the homology may be performed using a comparison program which is well-known in the art and homology between at least two sequences may be calculated by a percentage (%).

In another aspect, the present invention provides a pharmaceutical composition for skin regeneration or wound healing, containing the peptide or a polynucleotide encoding the peptide as an active ingredient; a use for skin regeneration or wound healing of the peptide; and a method for skin regeneration or wound healing including administering a therapeutically effective dose of peptide to a subject.

The term "treatment" used in the present invention means all actions for improving or beneficially changing symptoms for the wound by administering the pharmaceutical composition according to the present invention.

In the present invention, the "subject" refers to a subject requiring treatment of the wound, and more specifically, refers to human or non-human primates, and mammals such as mice, dogs, cats, horses, and cows.

The term "skin regeneration" used in the present invention refers to a series of reactions in which a skin tissue is reconstituted in response to an overall skin aging and an external stimulus induced in the skin, and as one example, exhibits skin whitening, skin elasticity improvement, and wrinkle improvement effects. The "skin whitening" refers to not only brightening skin tone by inhibiting the synthesis of a melanin pigment but also improving skin hyperpigmentation such as spots or freckles caused due to ultraviolet rays, hormones or heredity.

The term "wound" used in the present invention refers to a phenomenon in which the tissues are damaged by external stimuli and general wound healing is usually accompanied by processes such as degeneration and death of cells, planocytes from surrounding tissues, effusion of tissue liquids, and precipitation of fibrin and formation of granulation tissue. For the purpose of the present invention, the wound treatment refers to helping reconstitution into normal skin tissue by promoting the processes as described above. Meanwhile, the wound may preferably be a gash, but is not limited thereto.

According to one embodiment of the present invention, two kinds of peptides (peptide 1 and peptide 2) were prepared (see Example 1), and by treating the peptide, a production amount of collagen is increased to promote wound healing and melanin production and tyrosinase activity of a B16F10 melanoma cell line were inhibited to confirm an excellent whitening effect (see Examples 2 to 4). In addition, by using a scratch assay and an acute cut animal model to evaluate the migration ability of HaCaT cells, an excellent wound treatment effect (reduction of wound) of the peptide can be confirmed (see Examples 5 and 6), and the peptide may be widely used as an active substance and a skin whitening agent which can replace existing formulations for skin regeneration or wound healing.

Meanwhile, the peptide or the polynucleotide encoding the peptide of the present invention may be delivered to a pharmaceutically acceptable carrier such as a colloidal suspension, powder, saline, lipid, liposome, microspheres, or nanospheric particles. The peptide or the polynucleotide may form a complex with a carrier or associated with the carrier and may be delivered in vivo using a delivery system which is known in the art, such as lipids, liposomes, microparticles, gold, nanoparticles, polymers, condensation reagents, polysaccharides, polyamino acids, dendrimers, saponins, adsorption enhancers or fatty acids.

In addition, the pharmaceutically acceptable carrier includes lactose, dextrose, sucrose, sorbitol, mannitol, starch, acacia, rubber, calcium phosphate, alginate, gelatin, calcium silicate, microcrystalline cellulose, polyvinylpyrrolidone, cellulose, water, syrup, methylcellulose, hydroxybenzoate, propylhydroxybenzoate, talc, magnesium stearate, mineral oil, and the like, which are generally used in formulation, but is not limited thereto. Further, the pharmaceutical composition may further include lubricants, wetting agents, sweeteners, flavors, emulsifiers, suspensions, preservatives, and the like in addition to the ingredients.

For the purpose of the present invention, the pharmaceutical composition of the present invention may preferably contain the peptide of the present invention at a concentration of 1 to 500 ng/ml for the skin regeneration effect, but is not limited thereto as long as the concentration may predict an effective therapeutic effect without cytotoxicity.

The pharmaceutical composition of the present invention may be administered orally or parenterally (for example, intramuscularly, intravenously, intraperitoneally, subcutaneously, intradermally, or topically) depending on the intended method, and the dose varies according to the condition and weight of a patient, the degree of disease, a type of drug, and the route and time of administration, but may be suitably selected by those skilled in the art.

Particularly, in the case of using the pharmaceutical composition of the present invention as an dermal external preparation, the pharmaceutical composition may additionally contain an adjuvant which is commonly used in a dermatology field, such as any other ingredient commonly used in the dermal external preparation including a fatty substance, an organic solvent, a solubilizer, a thickener and a gelling agent, a softener, an antioxidant, a suspending agent, a stabilizer, a foaming agent, a perfume, a surfactant, water, an ionic emulsifier, a nonionic emulsifier, a filler, a sequestering agent, a chelating agent, a preservative, vitamins, a blocking agent, a wetting agent, essential oil, a dye, a pigment, a hydrophilic active agent, a lipophilic active agent or a lipid vesicle. Further, the ingredients may be introduced with amounts commonly used in the dermatology field. In addition, the pharmaceutical composition is provided as the dermal external preparation, but is not limited thereto, and may be a formulation, such as an ointment, a patch, a gel, a cream or a spray.

The pharmaceutical composition of the present invention is administered with a pharmaceutically effective dose. In the present invention, the "pharmaceutically effective dose" means a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a pathway of administration, and an emission rate, duration of treatment, and simultaneously used drugs and other elements well-known in the medical field. The pharmaceutical composition according to the present invention may be administered as an individual therapeutic agent or in combination with other therapeutic agents, simultaneously, separately or sequentially administered with existing therapeutic agents, and administered singly or multiply. It is important to administer an amount capable of obtaining a maximum effect with a minimal amount without side effects by considering all of the elements and the amount may be easily determined by those skilled in the art.

In particular, the effective dose of the pharmaceutical composition according to the present invention may vary according to age, gender, condition, and weight of the patient, absorption of active ingredients in the body, inactive rate, excretion rate, disease type, and combined drugs, and may be increased or decreased according to the route of administration, the severity of obesity, gender, weight, age, and the like.

Further, in yet another aspect, the present invention provides a health functional food/cosmetic composition for improving skin aging or wound, containing the peptide or a polynucleotide encoding the peptide as an active ingredient.

The term "improvement" used in the present invention means all actions that at least reduce parameters associated with a treated condition, for example, the degree of symptoms. At this time, the health functional food/cosmetic composition may be used simultaneously or separately with the drug for treatment before or after the onset of the related diseases for preventing or improving skin aging or wound.

In the health functional food composition of the present invention, the active ingredient may be added to the food as it is or may be used together with other food or food ingredients, and may be appropriately used according to general methods. A mixing amount of the active ingredients may be appropriately determined according to a purpose of use (for prevention or improvement) thereof. Generally, in preparation of foods or beverages, the composition of the present invention may be added with an amount of preferably 15 wt % or less and more preferably 10 wt % or less with respect to a raw material. However, in the case of long-term ingestion for the purpose of health and hygiene or health regulation, the amount may be below the above range.

The health functional food composition of the present invention may contain other ingredients as a required ingredient without specific limitation other than the active ingredient. For example, like a general beverage, various flavoring agents or natural carbohydrates may be added as an additional ingredient. Examples of the aforementioned natural carbohydrates include general sugars, such as monosaccharides, for example, glucose, fructose, and the like; disaccharides, for example, maltose, sucrose, and the like; and polysaccharides, for example, dextrin, cyclodextrin, and the like, and sugar alcohols, such as xylitol, sorbitol, and erythritol. As the flavoring agents other than the above examples, natural flavoring agents (thaumatin and *stevia* extract (e.g., rebaudioside A, glycyrrhizin, etc.) and synthetic flavoring agents (saccharin, aspartame, etc.) may be advantageously used. The ratio of the natural carbohydrate may be appropriately determined by selection of those skilled in the art.

In addition, the health food composition according to the present invention may contain various nutrients, vitamins, minerals (electrolytes), flavoring agents such as synthetic flavoring agents and natural flavoring agents, coloring agents and thickening agents (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of such additives may also be appropriately selected by those skilled in the art.

The cosmetic composition of the present invention may be prepared by any formulation which is generally prepared in the art and for example, may be formulated by a solution, a suspension, an emulsion, paste, gel, cream, lotion, powder, soap, a surfactant-containing cleanser, oil, powder foundation, emulsion foundation, wax foundation, spray and the like, but is not limited thereto. More particularly, the cosmetic composition of the present invention may be prepared by a formulation of emulsion lotion, nutrition lotion, nourishing cream, massage cream, essence, eye cream, cleansing cream, cleansing foam, cleansing water, pack, spray or powder.

The effective carrier contained in the cosmetic composition of the present invention may use a carrier which is generally used in the art depending on the formulation. When the formulation of the present invention is paste, cream, or gel, as a carrier ingredient, animal oil, vegetable oil, waxes, paraffins, starch, tragacanth, cellulose derivatives, polyethylene glycol, silicone, bentonite, silica, talc, zinc oxide, or the like may be used.

When the formulation of the present invention is the powder or the spray, as the carrier ingredient, lactose, talc, silica, aluminum hydroxide, calcium silicate, or polyamide powder may be used. Particularly, in the case of the spray, a propellant such as chlorofluoro hydrocarbon, propane/butane or dimethyl ether may be additionally included.

When the formulation of the present invention is the solution or the emulsion, as the carrier ingredient, a solvent, a dissolving agent, or an emulsifying agent is used, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or sorbitan fatty acid ester is included.

When the formulation of the present invention is the suspension, as the carrier ingredient, a liquid diluent such as water, ethanol, or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agarose or tragacanth may be used.

When the formulation of the present invention is the surfactant-containing cleanser, as the carrier ingredient, aliphatic alcohol sulfate, aliphatic alcohol ether sulfate, sulfosuccinate monoester, isethionate, imidazolinium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, or the like may be used.

The ingredients contained in the cosmetic composition of the present invention may contain ingredients which are generally used in the cosmetic composition in addition to the active ingredients and the carrier ingredients, and for example, may contain general adjuvants such as antioxidants, stabilizers, solubilizers, vitamins, pigments and fragrances.

Hereinafter, preferred Examples for helping in understanding of the present invention are proposed. However, the following Examples are provided for more easily understanding the present invention and the contents of the present invention are not limited by the following Examples.

EXAMPLES

Example 1. Preparation of Peptide

In Example 1, peptides in Table 1 below were prepared. Thereafter, the synthesized peptides were purified using a high-performance liquid chromatography (SHIMADZU Prominence HPLC) and a column used a Shiseido capcell pak C18 column (4.6×50 mm). Further, the mass of the synthesized peptide was confirmed using a mass spectrometer (HP 1100 series LC/MSD).

TABLE 1

| Number | Amino acid sequence |
|--------|---------------------|
| 1      | REGRT (SEQ. 1)      |
| 2      | REGRTREGRT (SEQ. 2) |

Example 2. Evaluation of Production Ability of Collagen of Human Dermal Fibroblasts Collagen is a main ingredient of skin connective tissues, and increased collagen expression is essential in wound healing such as a gash or skin regeneration. As a result, in Example 2, the production ability of collagen of human dermal fibroblasts (HDF) according to the treatment of the peptide (peptide 1) prepared in Example 1 was evaluated by an experimental method disclosed in the existing document (J. Biol. Chem. 1993 268(14): 9941-9944). First, the human dermal fibroblasts were cultured in a DMEM medium added with 10% fetal bovine albumin (FBS), and the cultured cells were divided into a 6-well plate at a concentration of $2\times10^5$ cell/well and cultured for 24 hours, and then the medium was replaced with 2% FBS. After 24 hours from this, the cells were treated with the peptide (100, 10, 1 ng/ml) of the present invention, and thereafter, an amount of procollagen secreted to the culture medium was measured by using a Procollagen Type I C-peptide (PIP) EIA Kit, RNA was extracted with a Trizol reagent, and then the expression of Col1A1 (collagen type I, alpha 1) mRNA of the human dermal fibroblasts was confirmed through real-time PCR. Meanwhile, a separately untreated group (Control) was used as a control group and a TGF-treated group (TGF-) was used as a positive control group.

Figure 2:
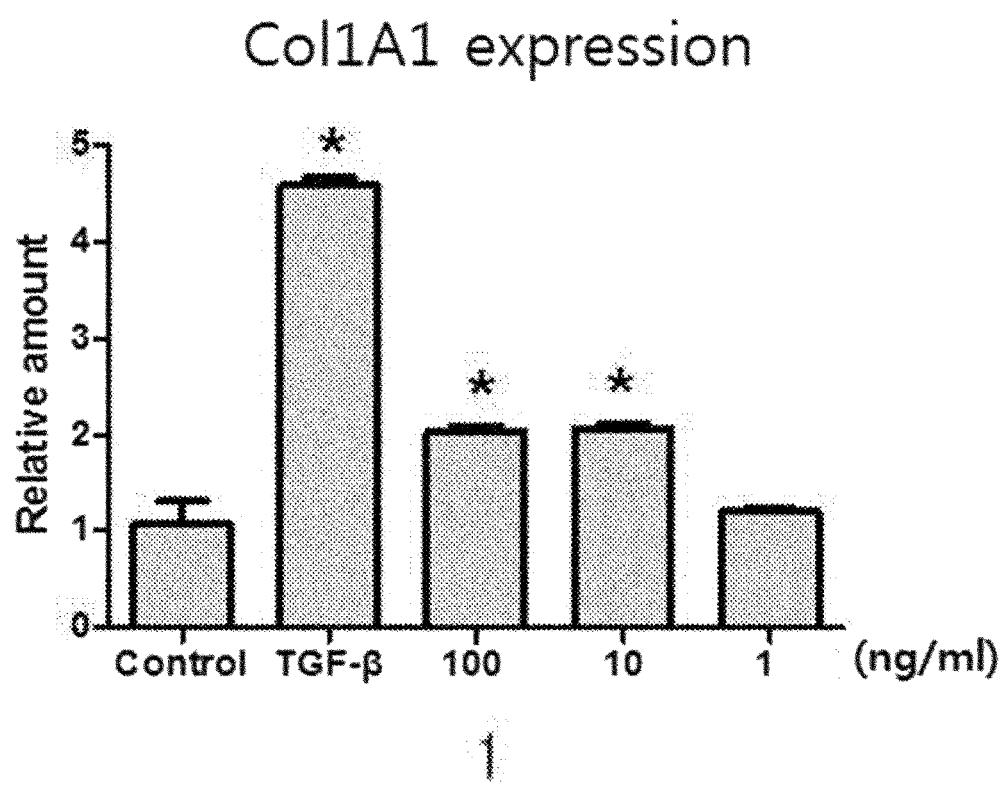
FIG. 2 illustrates a result of measuring an amount of Col1A1 produced from human dermal fibroblasts according to treatment of peptide 1 of the present invention.

As a result, as illustrated in FIGS. 1 and 2, it could be seen that in the group treated with the peptide of the present invention, a secretion amount of procollagen was increased compared to the control group and the TGF-treated group, and the expression of Col1A1 was significantly increased at a concentration of 10 ng/ml or more. From the result, it could be seen that the peptide of the present invention induced the generation of collagen to contribute to promotion of skin generation or wound healing.

Example 3. Evaluation of Production Ability of Melanin of Melanoma Cells

The color of the skin is determined by an amount of melanin pigment produced by melanoma cells, and many studies have been conducted to improve abnormal pigmentation of the skin. Particularly, excessive pigmentation caused by chronic gashes is considered as a major medical problem, but no definitive treatment method has yet been developed. Thus, in Example 2, the production ability of melanin of a melanoma cell line according to the treatment of the peptide (peptide 1) prepared in Example 1 was evaluated by an experimental method disclosed in the existing document (Life Sci. 2013 Aug. 14; 93(5-6):226-32). The melanoma cell line, B16F10 cells, was cultured in a DMEM medium added with 10% fetal bovine albumin, and the cultured cells were divided into a 12 well-plate at a concentration of $1\times10^5$ cells/well. After the culture for 24 hours, α-MSH (10 uM) promoting melanin synthesis and the peptide (1, 10, and 100 ng/ml) of the present invention were treated and cultured again for 24 hours, added with 200 µl of a 1N NaOH solution after washing each well with PBS, and then dissolved at 100° C. for 30 minutes. Thereafter, the absorbance was measured at 405 nm with an ELISA reader to confirm the amount of melanin produced from the melanoma cell line. Meanwhile, an untreated group was used as a control group and a α-MSH-treated group was used as a positive control group.

Figure 3:
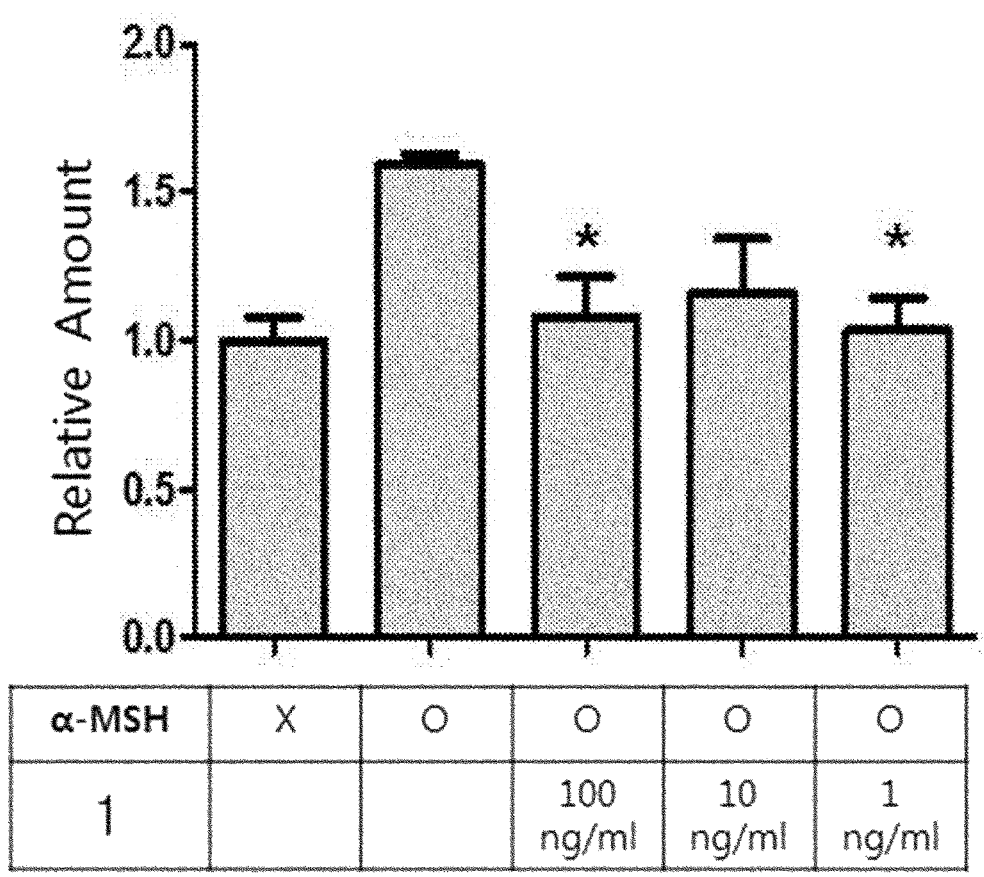
FIG. 3 illustrates a result of measuring an amount of melanin produced from melanoma cells according to treatment of peptide 1 of the present invention.

As a result, as illustrated in FIG. 3, a large amount of melanin was produced from the melanoma cell line in the α-MSH-treated group, whereas the production amount of melanin was greatly reduced in the group treated with the peptide of the present invention and particularly, there was no significant difference from a non-α-MSH-treated group. From the result, it could be seen that the peptide of the present invention had a skin whitening effect according to inhibition of melanin production.

Example 4. Evaluation of Tyrosinase Activity of Melanoma Cells

Tyrosinase as a rate-regulating enzyme that catalyzes the reaction in the melanin biosynthesis process was known to play a crucial role in regulating the amount of melanin in the cells. Thus, in Example 4, the tyrosinase activity of the melanoma cell line according to the treatment of the peptide (peptide 1) prepared in Example 1 was evaluated by an experimental method disclosed in the existing document (J. Dermatol. Sci. Vol. 57 (2010) 170-177). The melanoma cell line, B16F10 cells, was divided into a 12 well-plate at a concentration of $1\times10^5$ cells/well and cultured for 24 hours, and then treated with α-MSH (1M) and the peptide of the present invention (1, 10, 100 ng/ml), cultured for 24 hours again, and then was washed with PBS and suspended in a 50 mM phosphate buffer (pH 6.8) containing 1% Triton X-100 after washing each well with PBS. After vortexing, the cells was frozen at 80° C. for 30 minutes, dissolved at room temperature, and centrifuged at 1000 g for 10 minutes, and then 40 µl of a supernatant and 100 µl of 10 mM L-DOPA were added to a 96 well-plate and reacted at 37° C. Thereafter, the absorbance was measured at 405 nm with an ELISA reader to confirm the tyrosinase activity of the melanoma cell line. Meanwhile, a separate untreated group was used as a control group and a α-MSH-treated group and a Kojic acid-treated group were used as a positive control group.

Figure 4:
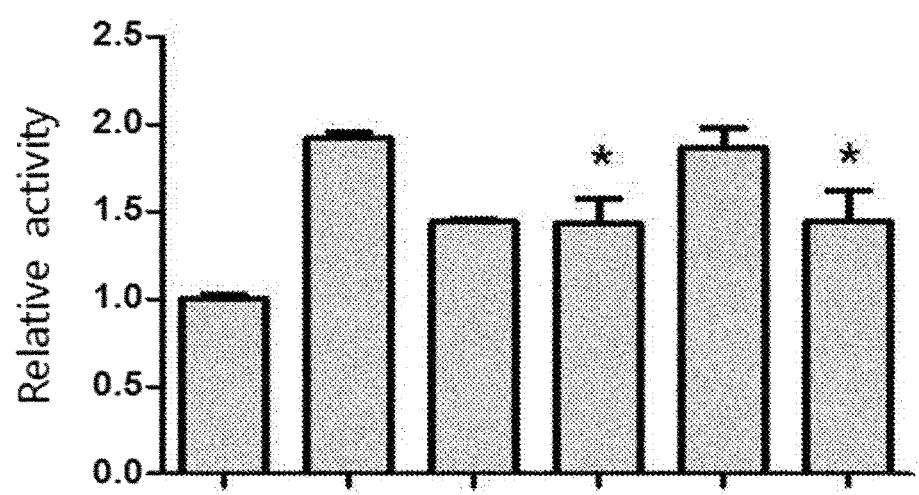
FIG. 4 illustrates a result of evaluating tyrosinase activity of melanoma cells according to treatment of peptide 1 of the present invention.

As a result, as illustrated in FIG. 4, the tyrosinase activity of the melanoma cell line was greatly increased in the α-MSH-treated group, whereas the enzyme activity was greatly reduced in the group treated with the peptide of the present invention and there was no significant difference from the Kojic acid-treated group having tyrosinase inhibition activity. From the result, it could be seen that the peptide of the present invention had a skin whitening effect according to inhibition of tyrosinase activity.

Example 5. Confirmation of Wound Treatment Effect Using In Vitro Wound Healing Model In Example 5, the wound treatment effect according to the treatment of the peptides (peptides 1 and 2) prepared in Example 1 was confirmed through a scratch assay. A human epithelial cell line, HaCaT cells was cultured for 2 hours by adding Mitomycin C (10 ug/ml) in a serum-free medium to induce scratch wound. After the cells were treated with the peptide (1 or 10 ng/ml) and TGF-β (1 ng/ml) as a positive control group in a medium added with 10% FBS, the migration ability of cells was observed over time and the reduction in wound size was quantified.

Figure 5:
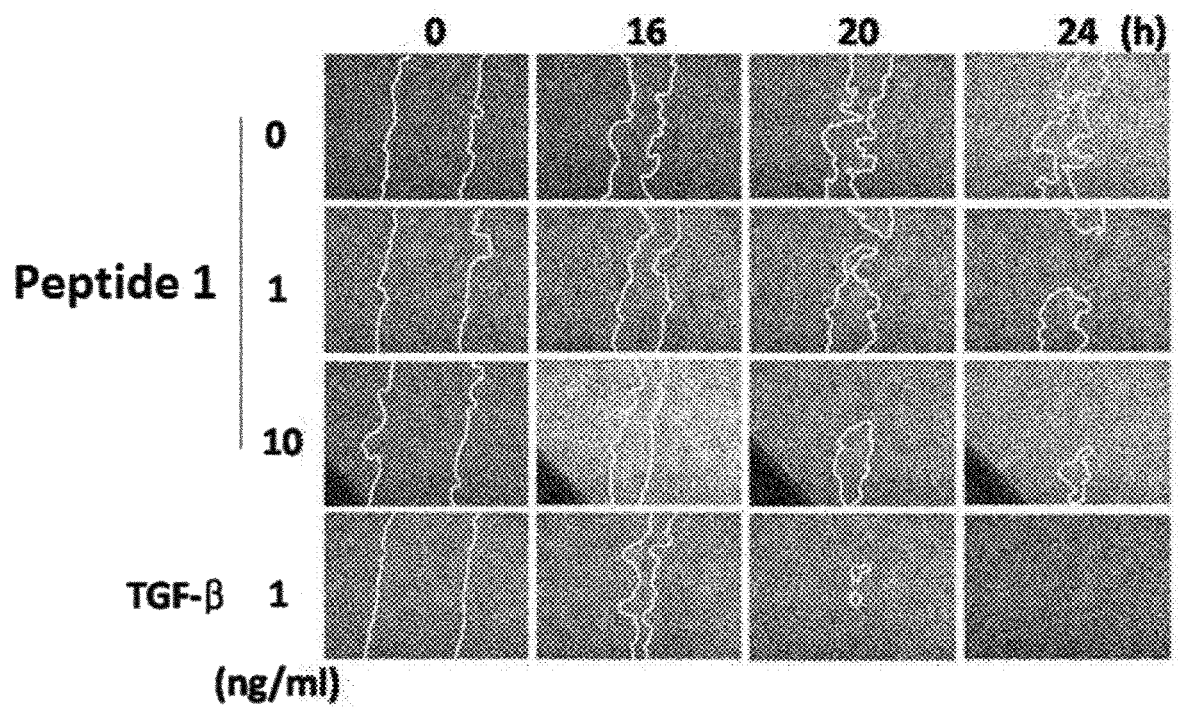
FIG. 5 illustrates a result of confirming a wound healing effect in an in vitro wound model according to treatment of peptide 1 of the present invention.
Figure 6:
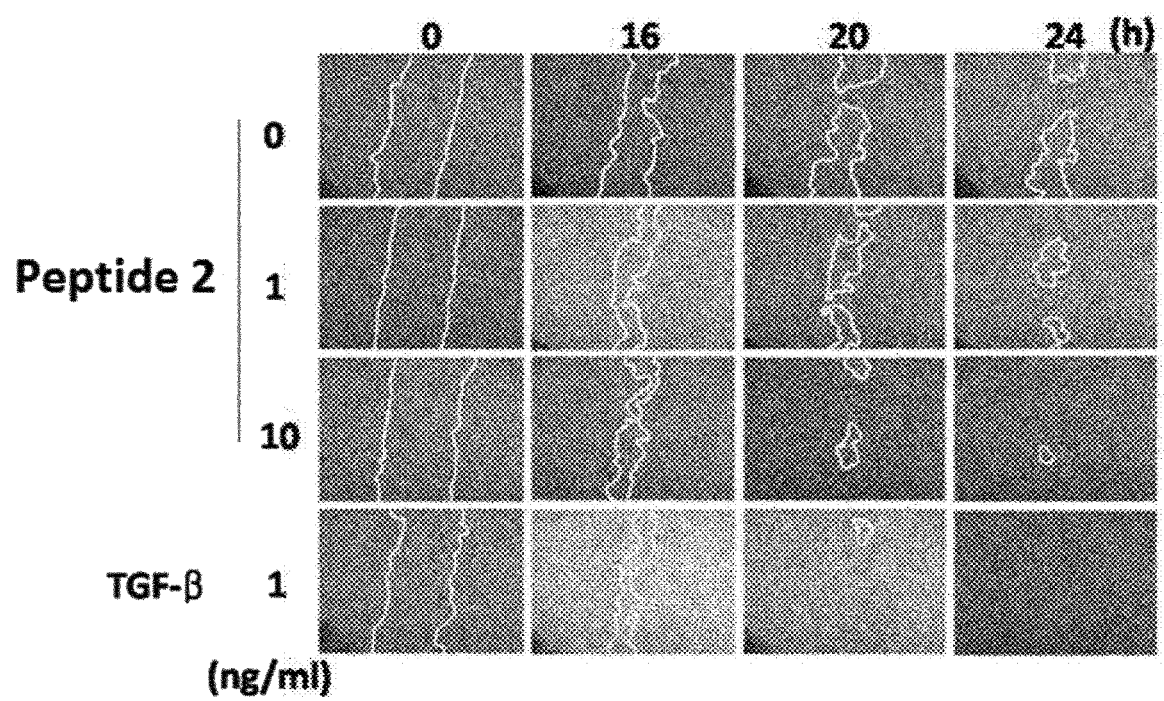
FIG. 6 illustrates a result of confirming a wound healing effect in an in vitro wound model according to treatment of peptide 2 of the present invention.
Figure 7:
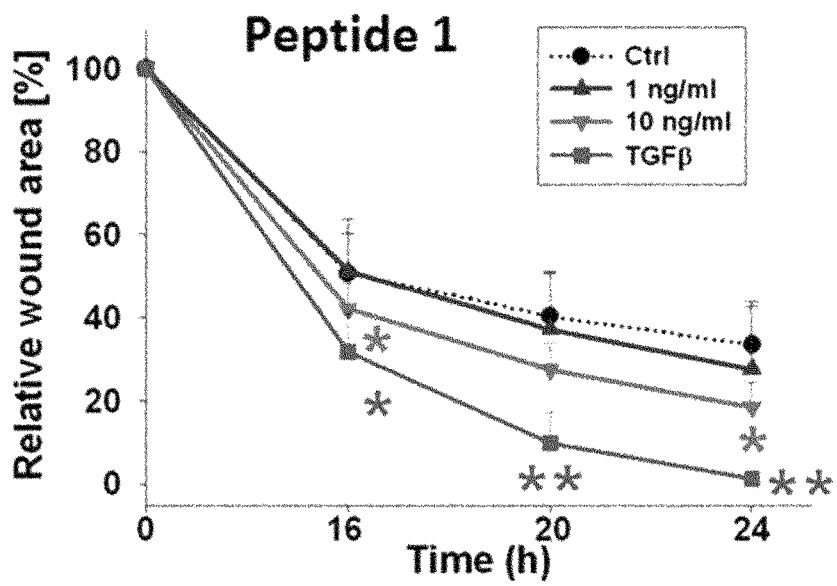
FIG. 7 illustrates a result of quantifying and evaluating a wound healing effect in an in vitro wound model according to treatment of peptide 1 of the present invention.
Figure 8:
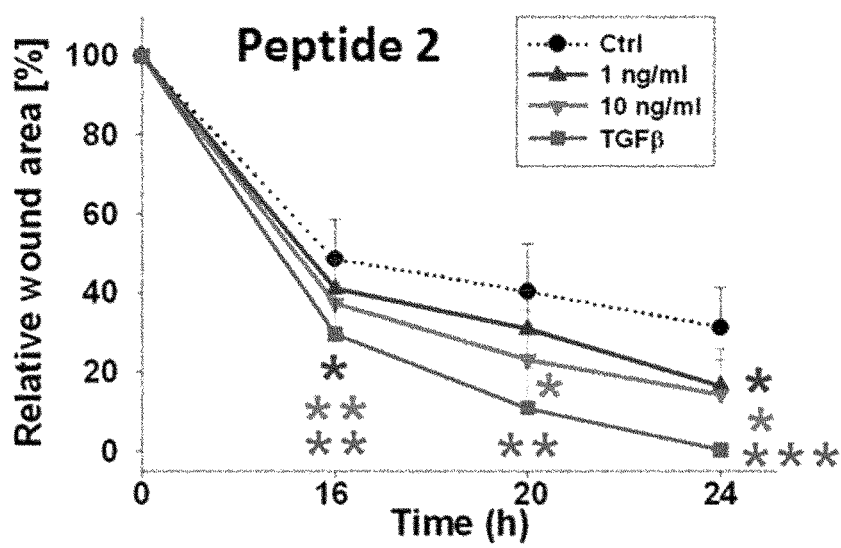
FIG. 8 illustrates a result of quantifying and evaluating a wound healing effect in an in vitro wound model according to treatment of peptide 2 of the present invention.

As a result, as illustrated in FIGS. 5 and 6, it was confirmed that the migration of HaCaT cells was increased in a peptide concentration-dependent manner in the group treated with the peptide of the present invention. Further, as the result of quantifying and evaluating the wound size, as illustrated in FIGS. 7 and 8, significant reduction of the wound size according to treatment of peptide 1 or peptide 2 was confirmed, and particularly, the effect of peptide 2 was more remarkable and a definite wound reduction effect was observed even at a relatively low concentration (1 ng/ml) as well as a high concentration (10 ng/ml).

Example 6. Confirmation of Wound Treatment Effect Using Acute Wound Animal Model In Example 6, the wound treatment effect according to the treatment of the peptides (peptides 1 and 2) prepared in Example 1 was confirmed in vivo using an acute wound animal model.

6-1. Confirmation of Change in Wound Size

After an 8-week-old Balb/c nude mouse was anesthetized with Avertin (2.5%), the skin of the animal's back was cut by using a circular punch having a 10 mm diameter to induce an acute wound. The peptide was treated (500 ng/one time) at the site of excision total 5 times at 24-hour intervals at the site of excision and reduction of the wound area over time was measured for 14 days and an EGF was used as a positive control group (10 ug/one time). In this case, the peptide was treated with 20% pluronic F-127 (PBS) in a mixture state and the wound sizes over time were measured and digitized using a digital camera and an ImageJ program and compared with each other.

Figure 9:
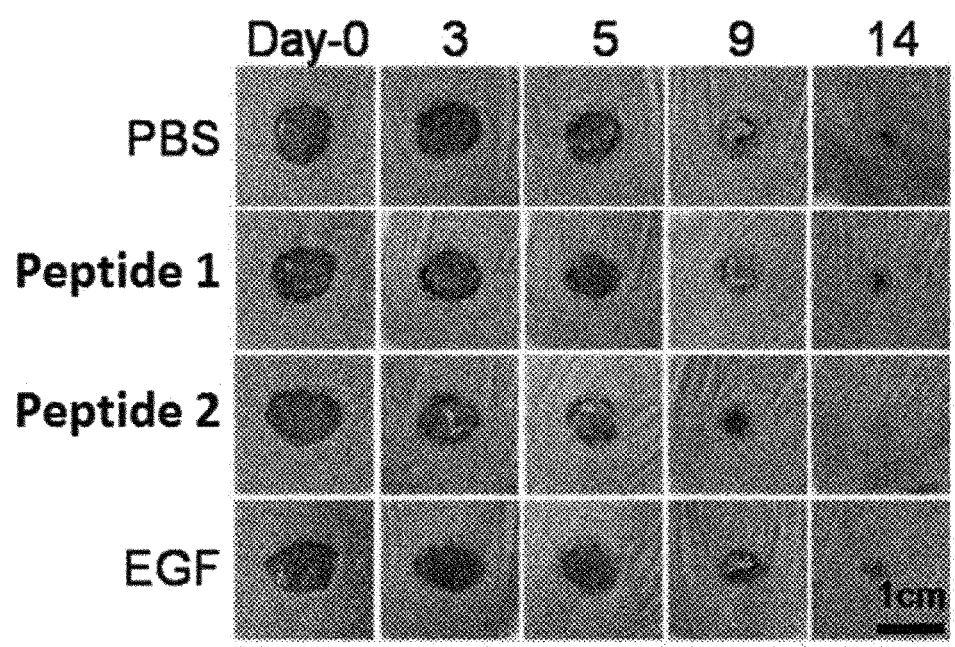
FIG. 9 illustrates a result of confirming a wound healing effect in an acute cut animal model according to treatment of peptide 1 or 2 of the present invention.
Figure 10:
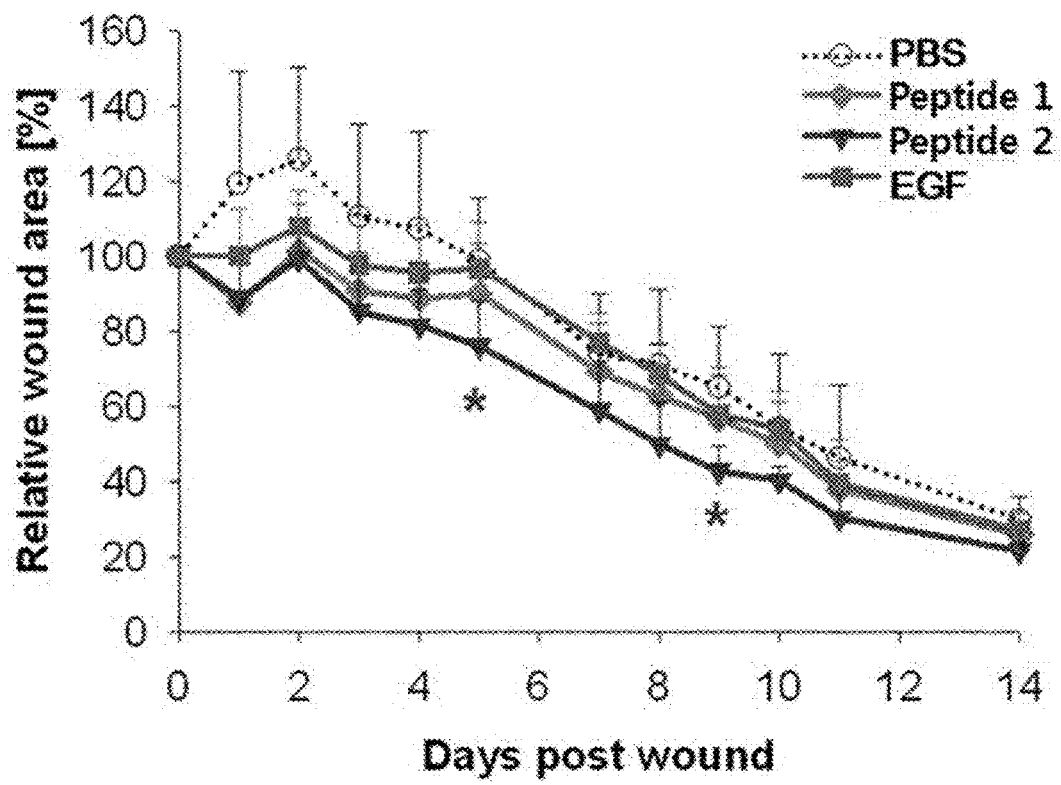
FIG. 10 illustrates a result of quantifying and evaluating a wound healing effect in an acute cut animal model according to treatment of peptide 1 or 2 of the present invention.

As a result, as illustrated in FIGS. 9 and 10, it could be seen that when peptide 1 or peptide 2 was treated, a reduction in wound size similar to or better than a positive control was obtained. In particular, since peptide 2 has a twice larger molecular weight as a dimeric form of peptide 1, even though the peptide 2 was treated at a lower concentration than that of peptide 1, it could be seen that the peptide 2 had an excellent effect as compared to the case treated with the peptide 1 and the excellent wound treatment effect even compared to a positive control group.

6-2. Confirmation of Histological Change

An acute wound was induced in the same manner as in Example 6-1, and the skin tissue was cut on 5 day after the acute wound was induced to prepare tissue fragments. Thereafter, histological changes according to peptide treatment were observed by H&E staining and observing the H&E staining by a microscope. Meanwhile, an EGF was used as a positive control group.

Figure 11:
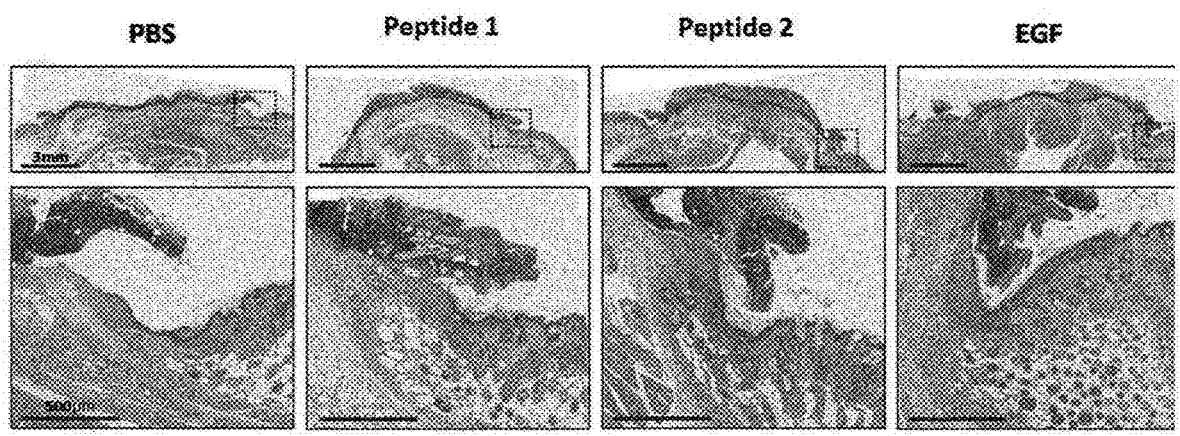
FIG. 11 illustrates a result of confirming a skin tissue change through H&E staining in an acute cut animal model according to treatment of peptide 1 or 2 of the present invention.

As a result, as illustrated in FIG. 11, in the tissues treated with peptide 1 and peptide 2, thicknesses of epidermis and dermis layers were larger than those of a PBS negative control group like a positive control group. In addition, epithelialization also actively progressed, and histological opinions related to wound healing or recovery were confirmed.

When summarizing the results, it can be seen that the peptides (peptide 1 and peptide 2) of the present invention may remarkably accelerate the wound recovery rate and may be used as an active substance for wound healing.

The aforementioned description of the present invention is to be exemplified, and it can be understood by those skilled in the art that the technical spirit or required features of the present invention can be easily modified in other detailed forms without changing. Therefore, it should be understood that the above-described exemplary embodiments are illustrative in all aspects and do not limit the present invention.

The invention claimed is:

1. A synthetic peptide selected from the amino acid sequence consisting of SEQ ID NO: 1 or the amino acid sequence consisting of SEQ ID NO: 2, wherein the N- or C-terminal of the synthetic peptide is attached to a protective group selected from the group consisting of an acetyl group, a fluorenylmethoxy carbonyl group, a formyl group, a palmitoyl group, a myristyl group, a stearyl group, a polyethylene glycol (PEG) group, a methyl group, an amide group, an albumin group, a polysialic acid (PSA) group, a hydroxyethyl starch (HES) group, and a C12-C18 fatty acid group.

2. A method for skin regeneration or wound healing, comprising the step of administering a composition comprising a pharmaceutically effective amount of a synthetic peptide or a polynucleotide encoding the peptide as an active ingredient to a subject or subject having a wound, wherein the synthetic peptide is selected from the amino acid sequence consisting of SEQ ID NO: 1 or SEQ ID NO: 2.

3. The method of claim 2, wherein the N- or C-terminal of the synthetic peptide is attached to a protective group selected from the group consisting of an acetyl group, a fluorenylmethoxy carbonyl group, a formyl group, a palmitoyl group, a myristyl group, a stearyl group, or a polyethylene glycol (PEG) group, a methyl group, an amide group, an albumin group, a polysialic acid (PSA) group, a hydroxyethyl starch (HES) group, and a C12-C18 fatty acid group.

4. The method of claim 2, wherein the peptide is contained at a concentration of 1 to 500 ng/ml.

5. The method of claim 2, wherein the wound is a gash.

6. The method of claim 2, wherein the composition further comprises a pharmaceutically acceptable carrier.

7. A method for improving skin aging or wound healing, comprising the step of administering a composition comprising a cosmetically effective amount of a synthetic peptide or a polynucleotide encoding the peptide as an active ingredient to a subject or subject having a wound, wherein the synthetic peptide is selected from the amino acid sequence consisting of SEQ ID NO: 1 or SEQ ID NO: 2.

8. The method of claim 7, wherein the N- or C-terminal of the synthetic peptide is attached to a protective group selected from the group consisting of an acetyl group, a fluorenylmethoxy carbonyl group, a formyl group, a palmitoyl group, a myristyl group, a stearyl group, or a polyethylene glycol (PEG) group, a methyl group, an amide group, an albumin group, a polysialic acid (PSA) group, a hydroxyethyl starch (HES) group, and a C12-C18 fatty acid group.

9. The method of claim 7, wherein the composition is in the form of suspension, emulsion, paste, gel, cream, lotion, powder, wax or spray.

10. The method of claim 7, wherein the composition has a skin whitening activity.

11. The synthetic peptide of claim 1, wherein the amino acid sequence consists of SEQ ID NO: 1.

12. A synthetic peptide with an amino acid sequence consisting of SEQ ID NO: 2.

13. A pharmaceutical composition comprising a synthetic peptide with an amino acid sequence consisting of SEQ ID NO: 2 and a pharmaceutically acceptable carrier.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: peptide 1

<400> SEQUENCE: 1

Arg Glu Gly Arg Thr
1               5

<210> SEQ ID NO 2
<211> LENGTH: 10
<212> TYPE: PRT
<213> ORGANISM: Artificial Sequence
<220> FEATURE:
<223> OTHER INFORMATION: peptide 2

<400> SEQUENCE: 2
```

```
Arg Glu Gly Arg Thr Arg Glu Gly Arg Thr
1               5                   10
```